(12) United States Patent
Winter et al.

(10) Patent No.: US 6,589,527 B1
(45) Date of Patent: *Jul. 8, 2003

(54) RETARGETTING ANTIBODIES

(75) Inventors: Gregory Paul Winter, Cambridge (GB); Kaspar Philipp Holliger, Cambridge (GB)

(73) Assignee: Medical Reseach Council, London (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/621,038

(22) Filed: Mar. 22, 1996

Related U.S. Application Data

(63) Continuation of application No. PCT/GB94/02019, filed on Sep. 16, 1994.

(30) Foreign Application Priority Data

Sep. 22, 1993 (GB) .............................................. 9319969
Dec. 3, 1993 (WO) ............................... PCT/GB93/02492
Jun. 17, 1994 (GB) .............................................. 9412166

(51) Int. Cl.[7] ....................... A61K 39/395; C07K 16/00
(52) U.S. Cl. ................................. 424/136.1; 530/387.3
(58) Field of Search ......................... 424/130.1, 178.1, 424/136.1; 435/7.2; 530/388.1, 809, 387.3

(56) References Cited

U.S. PATENT DOCUMENTS

| | | | |
|---|---|---|---|
| 4,946,778 A | 8/1990 | Ladner et al. | 435/69.6 |
| 5,534,254 A | 7/1996 | Huston et al. | 424/135.1 |
| 5,837,242 A | * 11/1998 | Holliger et al. | |

FOREIGN PATENT DOCUMENTS

| | | |
|---|---|---|
| WO | WO 88/09344 | 1/1988 |
| WO | WO 92/01047 | 1/1992 |
| WO | WO 93/11161 | 6/1993 |
| WO | WO 94/04691 | 3/1994 |

OTHER PUBLICATIONS

Holliger et al., "'Diabodies': Small Bivalent and Bispecific Antibody Fragments", Proceedings of the National Academy of Science, U.S.A., vol. 90, Jul. 1993, pp. 6444–6448.*

Clark et al., "Hybrid Antibodies for Therapy", in Monoclonal Antibody Therapy, Edited by H. Waldmann, published by Karger, New York, 1988, pp. 31–49.*

(List continued on next page.)

Primary Examiner—David Saunders
(74) Attorney, Agent, or Firm—Nixon & Vanderhye P.C.

(57) ABSTRACT

Antibodies are retargeted to a target for which they have no functional specificity under normal circumstances. Use is made of a multi-specific binding substance which has binding specificity for the target and anti-antibody binding specificity. The binding substance may comprise an immunoglobulin antigen binding site and may be a "diabody". Depending on the antibody bound, effector functions such as Complement, ADCC and immune blocking are recruited to act on the target. Example targets are human cells. In vivo and in vitro utilities are exemplified, including lysis of tumor cells and agglutination of red blood cells.

15 Claims, 2 Drawing Sheets

OTHER PUBLICATIONS

Figure 1:
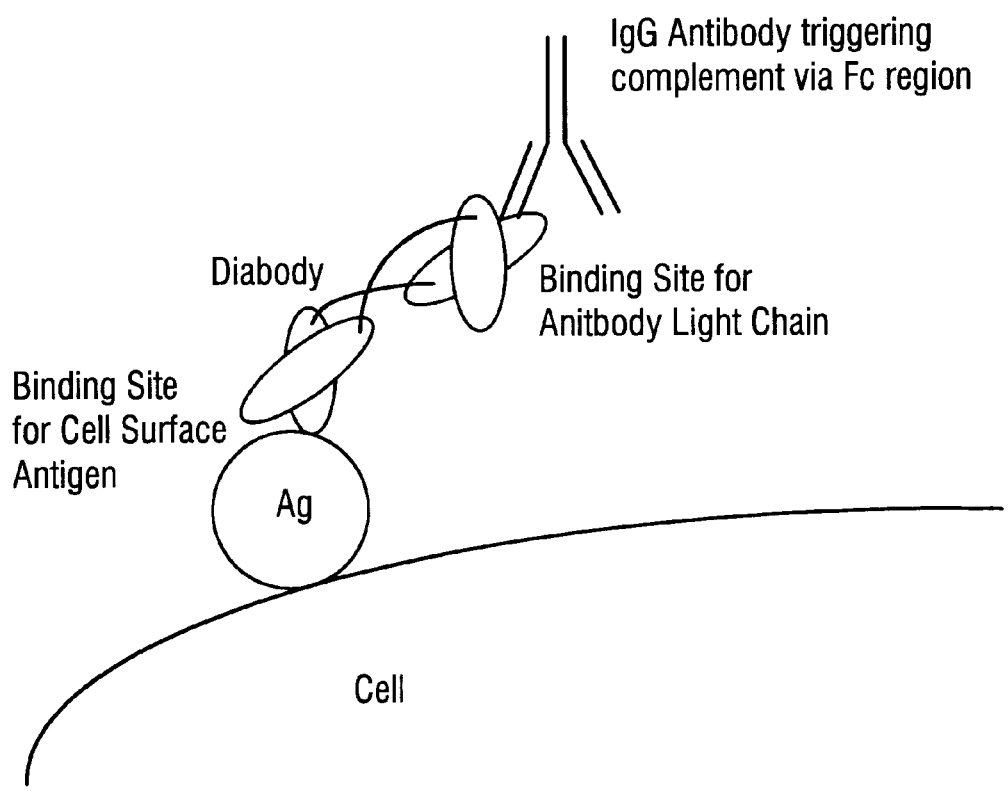

Bruggemann et al., "Comparison of the Effector Functions of Human Immunoglobulins Using a Matched Set of Chimeric Antibodies", Journal of Experimental Medicine, vol. 166, Nov., 1987, pp. 1351–1361.*

Riechmann et al., "Reshaping Human Antibodies for Therapy", Nature, vol. 332, Mar. 24, 1988, pp. 323–327.*

Harris et al., "Therapeutic Antibodies–The Coming of Age", Tibtech, vol. 11, Feb. 1993, pp. 42–44.*

R. Dillman, "Antibodies as Cytotoxic Therapy", Journal of Clinical Oncology, vol. 12, No. 7, Jul. 1994, pp. 1497–1515.*

Brissinck et al., "Treatment of Mice Bearing BCL, Lymphoma With Bispecific Antibodies," *J. Immunol.,* 147(11):4019–4026 (1991).

Chiswell et al., "Phage antibodies: Will new 'coliclonal' antiobodies replace monoclonal antibodies," *Trends in Biotechnology* 10(3):80–84 (Mar. 1992).

Condra J.H. et al., "Bacterial Expression of Antibody Fragments That Block Human Rhinovirus Infection of Cultured Cells," *J. Biol. Chem.,* 265(4):2292–2295 (Feb. 5, 1990).

Griffiths, A.D. et al., "Human anti–self with high specificity from phage display libraries," *EMBO J.,* 12(2):725–734 (1993).

Huston et al., "Protein Engineering of Single–Chain Fv Analogs and Fusion Proteins," *Methods in Enzymology,* 203:46–89 (1991).

Lodish et al., (Eds.) In *Molecular Cell Biology,* Third Edition, Scientific American Books, W.H. Freeman and Company, New York, Chapter 27, pp. 1304 (1995).

Titus et al., "Human T Cells Targeted With Anti–T3 Cross–Linked To Antitumor Antibody Prevent Tumor Growth In Nude Mice," *J. Immunol.,* 138(11):4018–4022 (1987).

Waldmann, H. (ed.): in Monoclonal Antibody Therapy, vol. 45, S. Karger AG, Basel (Switzerland), pp. 44–45 (1988).

Weiner et al., "The Role of T Cell Activation in Anti–CD3 x Antitumor Specific Antibodiy Therapy," *J. Immunol.,* 152:2385–2392 (1994).

Whitlow et al., "An improved linker for single–chain Fv with reduced aggregation and enhanced proteolytic stability," *Protein Engineering,* 6(8):989–995 (1993).

* cited by examiner

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 5 amino acids
      (B) TYPE: amino acid
      (C) STRANDEDNESS: single
      (D) TOPOLOGY: linear (xi) SEQUENCE DESCRIPTION: SEQ ID NO: 1:

Gly Gly Gly Gly Ser
1          5

(2) INFORMATION FOR SEQ ID NO: 2:

(i) SEQUENCE CHARACTERISTICS:
      (A) LENGTH: 57 base pairs
      (B) TYPE: nucleic acid
      (C) STRANDEDNESS: single
      (D) TOPOLOGY: linear (xi) SEQUENCE DESCRIPTION: SEQ ID NO: 2:

CATGCCATGA CTCGCGGCCC AGCCGGCCAT GGCCSAGGTG AAGCTGGTGG ARTCTGG    57

(2) INFORMATION FOR SEQ ID NO: 3:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO: 3:

```
GAGCCATCAA TCGATCTGGT CACCGTCTCC TCAGGCGGTG GCGGATCGGA CATTGTGCTR      60

ACCCAGTCTC CA                                                          72
```

(2) INFORMATION FOR SEQ ID NO: 4:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO: 4:

```
GACTCATTCT CGACTGAGCT CACTTGGCGC GCCTTATTAC CGTTTGATCT CGAGCTTGGT      60

CCC                                                                    63
```

(2) INFORMATION FOR SEQ ID NO: 5:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO: 5:

```
GTCCTCGCAA CTGGCGCGCC ACAATTTCAC AGTAAGGAGG TTTAACTTGT GAAAAAATTA      60

TTATTCGCAA TT                                                          72
```

(2) INFORMATION FOR SEQ ID NO: 6:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO: 6:

```
GAGCCATCAA TCGATCTGGT CACCGTCTCC TCAGACATTG AGCTCACCCA GTCTCCA         57
```

(2) INFORMATION FOR SEQ ID NO: 7:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO: 7:

```
GAGCCATCAA TCGATCTGGT CACCGTCTCC TCAGGCGGTG GCGGATCGGA CATTGAGCTC      60

ACCCAGTCTC CA                                                          72
```

(2) INFORMATION FOR SEQ ID NO: 8:

(i) SEQUENCE CHARACTERISTICS:
        (A) LENGTH: 59 base pairs
        (B) TYPE: nucleic acid
        (C) STRANDEDNESS: single -continued (D) TOPOLOGY: linear (xi) SEQUENCE DESCRIPTION: SEQ ID NO: 8:

GAGCCATCAA TCTCGGAGCT CGATGTCTGA GGAGACGGTG ACCGTGGTCC CTTGGCCCC        59

(2) INFORMATION FOR SEQ ID NO: 9:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (xi) SEQUENCE DESCRIPTION: SEQ ID NO: 9:

GAGCCATCAA TCTCGGAGCT CGATGTCCGA TCCGCCACCG CCTGAGGAGA CGGTGACCGT        60

GGTCCCTTGG CCCC        74

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 10:

GTCGTCTTTC CAGACGTTAG T        21

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 11:

GTAAAACGAC GGCCAGT        17

(2) INFORMATION FOR SEQ ID NO: 12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 12:

CAGGAAACAG CTATGAC        17

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 13:

GGTTATGGTG ACTTTCTCCC C        21

RETARGETTING ANTIBODIES

CROSS-REFERENCE TO RELATED APPLICATION

This is a continuation of International Application No. PCT/GB94/02019 filed Sep. 16, 1994.

The present invention relates to retargetting of antibodies to a site or antigen for which they have no functional specificity under normal circumstances. A method is described employing an antigen-specific binding substance which possesses at least two specificities; one specificity for the target site, the other capable of binding to part of an antibody molecule. In this manner, antibodies with no specificity for the antigen target may be brought into proximity with the antigen via the antigen-specific binding substance. This principle is advantageous for re-targeting antibodies in the circulation to sites of disease within the body, e.g. tumours or sites of is viral, bacterial or parasitic infection or combinations thereof. This principle may also be applied to block inappropriate immune responses exemplified by autoimmune disease or hypersensitivity reactions. Retargetting can be achieved with conventional bispecific antibodies, e.g. prepared chemically or from hybrid hybridomas, or using the novel bispecific antibody fragments, diabodies (P. Holliger et al Proc. Natl. Acad. Sci. USA 90 6444–6448, 1993 and PCT/GB93/02492).

Antibodies are proteins elaborated by B-lymphocytes to play a key role in the specific arm of the vertebrate immune system. This arises from their collective capacity to bind to an enormous diversity of antigen structures, with individual antibody molecules capable of precise specificity for their cognate antigen. The bulk of the antibody population is found in abundance in the blood and interstitial fluids, with minor types located at mucosal surfaces such as the intestinal lumen. An antibody binding to a foreign organism or a tumor cell marks it for destruction by the antibody encoded effector functions of the immune system. Destruction may be effected by either the complement cascase or antibody directed cell-mediated cytotoxicity (ADCC). ADCC is mediated through binding of antibody Fc regions to their Pc receptors on e.g. macrophages, eosinophils, K cells but also basophils and mast cells. Interaction with Fc receptors mediates not only cytolysis but also phagocytosis and immune clearance. Ig isotypes differ markedly in the spectrum of effector functions they recruit.

The immune system operates natural checks and balances to prevent production of antibodies with specificity for the host, so-called 'self-antigens'. occasionally, the system breaks down causing autoimmune disease. Self-tolerance is one reason why the immune system may not destroy tumours and other malignancies, since these derive from host cells growing abnormally.

It has proved possible to use antibodies in medical intervention, using antibodies manufactured outside the body. Techniques for immortalisation of B-lymphocytes has enabled manufacture of monoclonal antibodies for a range of commercial applications in science and human healthcare (Clinical Applications of Monoclonal Antibodies, E. S. Lennox, Ed. British Medical Bulletin 1984. Churchill-Livingstone). Moreover, an understanding of the genetic and physical structure of antibodies has enabled their manipulation outside of the immune system, through the use of molecular biology techniques, especially using phage display technology (WO 92/01047; WO 92/20791; WO 93/06213; WO 93/11236; WO 93/19172; WO 94/13804).

Structurally, the simplest antibody (IgG) comprises four polypeptide chains inter-connected by disulphide bonds. The light chains exist in two different forms called kappa (K) and lambda (X). Each chain has a constant region (C) and a variable region (V). Each chain is organised into a series of domains. The light chains have two domains, one corresponding to the C-region (CL) and the other to the V-region (VL). The heavy chains have four domains, one V-region domain (VH) and three C-region domains, CH1, CH2 & CH3. The basic IgG antibody is Y-shaped; the two arms (tip of the Y, each being an 'Fab' region) contain a VH and a VL domain associated with one another. It is this pair of V-regions that differ from one antibody to another (owing to amino acid sequence variations), and which together are responsible for recognising the antigen and providing an antigen binding site (ABS). In even more detail, each V-region (whether heavy chain or light chain) consists of three complementarity determining regions (CDRs) separated by four framework regions (FR) The CDR's are the most variable part of the variable regions, and they perform the critical binding function. The CDR regions are derived from many potential germline sequences via a complex process involving recombination, mutation and selection.

It has been shown that the function of binding antigens can be performed by fragments of a whole antibody. Example binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544–546 (1989)) which consists of a VH domain; (v) isolated CDR regions; (vi) F(ab')2 fragments, a bivalent fragment comprising two linked Fab fragments (vii) bispecific single chain Fv dimers (PCT/US92/09965) and (viii) diabodies, bivalent or bispecific fragments constructed by gene fusion (P. Holliger et al, supra; WO 94/13804. Diabodies are discussed further infra. Bispecific fragments are especially well suited to the current invention.

Whereas the V-domains (and fragments containing V-domains) are largely responsible for interacting with antigen, the C-domains recruit effector functions. The type of effector function recruited is largely governed by the class of C-domain (the isotype; M. Bruggemann et al J. Exp. Med. 166 1351 1987; L. Riechmann et al Nature 332 323 1988; J. Greenwood et al Eur. J. Immunol. 23 1098–1104 1993). In this way, antibodies, which have evolved to combat pathogens, bind to antigens on the pathogen and in so doing initiate an appropriate immune response aimed at destroying the invader. For example, C-domains of the IgG1 (γ1) isotype can kill cells by triggering the complement cascade at the cell surface, resulting in lysis, or through binding C-domain receptors (Fc receptors) on specialised phagocytic and killer cells through ADCC. On another hand, antibodies of the IgG4 isotype (γ4) appear actively to block a response. In the context of the present application this blocking is considered to be an effector function which can be recruited to a chosen target. The binding sites for complement and Fc receptors map to the CH2 domain, sequence variation between CH2 domains of the different isotypes results in different strengths of interaction with complement and Fc receptors. All isotypes except IgE require that the C-domain is correctly glycosylated.

By association of the V-region with a given C-region isotype, an appropriate immune response can be triggered when the antibody binds to antigen. Because the type of immune response is governed by the isotype, artificially-made antibodies can be endowed with appropriate constant regions to be used therapeutically, for example to destroy tumour cells (Hale, G et al., Lancet ii, 1394–1399 (1988)).

If an antibody is to be used in such a way that requires recruitment of natural effector functions, then the antibody (except for the IgE isotype) must be manufactured in eukaryotic cells in order that the protein is glycosylated. Unfortunately, the type and extent of glycosylation varies with eukaryotic cell-type and culture conditions (Borys, M. C. et al., Biotechnology 11, 720–725 (1993)), and this can dramatically shorten their longevity in the circulation as well as adversely influencing recruitment of effector functions. There is the added risk that an inappropriately glycosylated antibody will be immunogenic, limiting the duration of the therapy.

One way of circumventing the need for correctly glycosylated constant regions is to manufacture antibodies comprising at least two different antigen-binding sites. These are known as bispecific antibodies and they can be manufactured in a variety of ways (Holliger, P. and Winter G. Current Opinion Biotechnol. 4, 446–449 (1993)). Again using tumour killing as an example, one antigen binding site is directed against a tumour marker whereas the other can be directed against an antigen present on an effector cell-type. Bispecific antibodies incorporating a specificity for the T-cell co-receptor CD3 have been shown to inhibit tumour growth (Titus, J. A. et al., J. Immunol. 138, 4018–4022 (1987)) and to cure lymphoma (Brissinck J. et al, J. Immunol. 174, 4019–4026 (1991)). In this way the interaction between Fc region and effector cell is replaced by direct interaction between one of the antigen binding sites and the effector. Diabodies directed against carcinoembryonic antigen (CEA; a human tumour cell marker) and CD16 (on human T lymphocytes) have been demonstrated to mediate lysis of human tumour cells on addition of peripheral blood lymphocytes (WO 94/13804).

The present applicants have realised that the direct interaction between the C-region of the antibody molecule and the effector results in limited activation of the immune system, and that it would be advantageous to activate (or indeed shut down) immune responses at a given target to a much greater degree. The applicants have further realised that such modulation may be achieved by redirecting naturally occurring antibodies to a site or target for which they do not necessarily possess specificity. The present applicants have realised in addition that this principle may be brought into effect through the use of binding substances which possess two or more specificities. One of many examples is a bispecific antibody which incorporates specificity for other antibodies. An antibody with specificity for a tumour cell and, for example, IgG1 constant regions will bind to the tumour in situ and accumulate IgG1 antibodies present in the circulation, such that IgG1-specific effector functions are called down at the tumour site. Antibodies in the serum of an individual are native to that person and therefore will be functional in activating complement or ADCC. The principle of indirect recruitment is beneficial over direct interaction with effector cells for several main reasons.

Firstly, there is evidence for the existence of antibody networks in the immune system, in which naturally occurring anti-antibody specificities build a branching mass of antibodies upon and around antibodies complexed at a target site (A. S. Perelson Immunol. Rev. 110 5–36 1989; antibody networks are reviewed in N.J. Calvanico Dermatol. Clin. 11 379–389 1993). It is thought that this serves to amplify the effect of binding a few molecules of antibody to a target such that a small degree of specific binding can trigger a disproportionately large effector response. This contrasts with direct binding to effector cells or triggering of complement, since in this instance binding is stoichiometric (one antibody per antigen at most) rather than multiplicative.

A second reason why this arrangement is beneficial relates to control of serum half-life. Correctly glycosylated antibodies have fairly reliable serum clearance rates, the rate of turnover being different for different isotypes. For example IgG1 has a serum half life in the order of 21 days, whereas on the other hand, IgG3 and IgE are turned over in a matter of 1–2 days. The duration of the therapeutic effect may be controlled by the half-life of the administered bispecific antibody, e.g. diabody. The half-life is likely to depend on its binding affinity (and kinetics) for the targetted antibody and antigen and on the serum concentration of the antibody target.

Thirdly, this approach can be used in site-specific immunosuppression. Some antibodies, such as IgG4, actively prevent immune responses by blocking the epitopes. Indeed, some parasites are known exploit this property to escape immune attack (A. Capron et al Mem. Inst. Oswaldo Cruz 87 Suppl.5 1–9 1992), their antigens inducing antibody production of the correct specificity but with C-region isotypes incapable of inducing killing. This principle can be extended within the scope of the present invention to uses such as alleviation of autoimmune disorders such as rheumatoid arthritis and myasthenia gravis. In this case the bispecific antibody has specificity for the target epitope and for example, IgG4. However, patients may need to be screened for the ability of their immunoglobulin IgG4 to recruit effector functions, since the ability to do this appears to vary between individuals (Greenwood et al, supra).

Fourthly, in vivo, the individual's natural allotypes are recruited so the need for matching the individual's and the therapeutic antibodies allotypes is eliminated.

It will be clear to those skilled in the art that there exist many ways of putting this principle into operation. For example, naturally occurring or genetically engineered binding substances other than antibodies could be incorporated into a multiply-specific substance described herein. Examples include lectins, Fc-binding proteins such as-protein A or protein G, receptors such as Fc receptors and components from the complement system. Small molecules such as peptides, nucleic acids or naturally-occurring, partially synthetic or synthetic chemicals can also be used. The aforementioned can be used in any order, number and combination to create multiply-specific is substances described herein for use in therapy, diagnosis and scientific research. However, the use of antibody or a fragment thereof is preferred. Especially preferred are antibody fragments such as (Fab)$_2$ and-diabodies lacking Fc regions, for reasons explained below. It should also be noted that, unless the context demands otherwise the term antibody is used herein (and commonly in the art) to include antibody fragments, both synthetic and naturally occurring, i.e. molecules comprising an immunoglobulin binding domain.

In the preferred embodiment, the multiply-specific substance described herein is a bispecific antibody capable of binding to an appropriate antibody isotype. "Diabodies" may be particularly advantageous for the purpose since they can be readily constructed and expressed in E.coli. Diabodies of appropriate binding specificities can be readily selected using phage display (WO 94/13804) from libraries. If one arm of the diabody is to be kept constant, for instance, with a specificity directed against an immunoglobulin light chain, then a library can be made where the other arm is varied and an antibody of appropriate specificity selected.

Although any type of bispecific antibody molecule could be used for retargetting antibodies, it is preferable to use (Fab)$_2$, scFv dimers or diabodies rather than whole antibodies. The presence of Fc in whole antibody may cause complications in vivo arising from direction to non-specific sites, especially to Fc receptors. Diabodies can be constructed without Fc, using only variable domains, avoiding this potential problem. In vitro, the simplicity of making bispecific diabodies, as opposed to bispecific whole antibodies, makes them the antibody form of choice.

One aspect of the present invention provides a method of recruiting an antibody mediated effector function to a target, the method employing a multi-specific binding substance having anti-antibody binding specificity and binding specificity for a target. This is illustrated in FIG. 1. Binding of the multi-specific binding substance to the target and to antibody allows recruitment of antibody-mediated effector function to the target. The binding substance is bound to antibody and to the target where it mediates the effector function of the antibody, generally, the effector function is the natural one of the bound antibody (e.g. ADCC, complement fixation or blocking, as discussed). The antibody may be any isotype, e.g. IgG1, IgG2, IgG3, IgG4, IgM, IgA, IgD, IgE, for recruitment of associated effector functions. Preferably the anti-antibody binding specificity of the binding substance is for the constant region of antibodies of one or more isotypes. Use of isotype-specific anti-antibody binding specificity enables choice of effector function recruited.

Human IgG1, IgG3 and IgM are particularly valuable for complement fixation and IgG1 and IgG3 are particularly valuable for ADCC. Then, the multi-specific binding substance will have binding specificity for a constant region of the isotype. IgM molecules are particularly useful in agglutination assays. IgG4 is the most suitable isotype for blocking antibodies, since it does not in general recruit antibody directed cellular cytotoxicity or complement. It may be valuable in some cases to use an isotype which does not activate complement to too great an extent, to prevent a toxic response. For recruitment of phagocytosis, IgG1 may be particularly suitable. Mast cells may be recruited via IgE antibodies. This may make them of value for cancer cell killing, but may limit their use for other applications (WO 92/11031).

Specificity directed against light chains allows recruitment of a spectrum of antibody isotypes including those which activate complement or ADCC.

Anti-idiotype specificity may be used. Specificities for widely found idiotypes such as that which may be provided by the commonly used DP-47 V gene germline sequence may be used to recruit any antibody where that idiotype is still recognisable in the mature antibody. Specificity for idiotypes of specific antibodies is useful for using the antibody displaying that idiotype in an agglutination assay. To use diabodies as an example, a diabody molecule directed against a cell surface marker and the idiotype of the antibody would bridge one cell to the antibody. A second diabody molecule would be able to bind to another antigen binding site on the antibody and to a second cell thus crosslinking them. IgM molecules would be particularly suitable for this, because they have 10 antigen binding sites per molecule.

The multi-specific binding substance may be bi-specific. It may be a bi-specific antibody or antibody fragment (as discussed). Preferably, it is a "diabody", ie a multimer (e.g. dimer) of polypeptides each of which have a first domain comprising a binding region of an immunoglobulin heavy chain variable region and a second domain comprising a binding region of an immunoglobulin light chain variable region, the two domains being linked but not able to associate to form an antigen binding site. The linkage may be by a peptide linker of −1 to about 10 amino acids (e.g. 5). The polypeptides associate into multimers wherein the first domain of one polypeptide associates with the second domain of another polypeptide to form an antigen binding site. For further information and possibilities of formats for a "diabody" for use in the present invention, refer to WO 94/13804. Also preferred are scFv dimers, wherein each polypeptide comprises heavy and light chain variable region binding regions which can associate intra-molecularly to form antigen binding site (in contrast to diabodies) because the peptide limber joining the two domains in each polypeptide is long enough, and (Fab)$_2$.

A method according to the present invention may be carried out in vitro or in vivo where it may be a method of treatment of an individual for a condition wherein recruitment of antibody mediated effector function is, or is likely to be, of benefit. Administration to an individual may be using any standard technique, the criteria for selection of a technique and selection of dosages, frequency of administration etc, being well known to those skilled in the art. Administration of antibody is described, for example, in Hale et al, *Lancet*, ii, 1394–1399 (1988), Simmons et al, *Circulation*, 89, 596–603 (1994) and Riethmuller et al, *Lancet*, 343, 1177–1183 (1994).

In vitro, use may be made of a multispecific binding substance, such as a bispecific antibody such as a diabody, in retargetting antibodies to recruit antibody effector function to treat target cells/tissue removed from a patient. For instance, bone marrow from a patient with leukaemia may be taken and the cells treated, ex vivo, with a binding substance such as a bispecific diabody directed against a marker specific for the tumour cells and an immunoglobulin IgG1 constant region, together with IgG1 antibody and complement. Tumour cells would then be specifically lysed and the whole cells remaining may be taken and returned to the patient. Alternatively, ADCC may be used, the binding substance (e.g. diabody) together with IgG1 and a preparation of killer cells being added to the bone marrow cells to lyse the tumour cells before returning the remaining cells to the patient.

Similarly, e.g. using complement lysis, the recruitment of effector function may be used in a diagnostic assay for the number of cells expessing a particular marker, e.g. tumour specific antigen, present in a sample e.g. of blood. The degree of lysis would reflect the number of cells present. If an anti-IgM binding substance (e.g. diabody) plus IgM were used, the increased complement lysis would increase the sensitivity to detect very small numbers of tumour cells expressing cell surface markers.

Mediation of effector function may be caused or allowed according to conditions under which the invention is operated. For instance, in vitro mediation may be caused by addition into the medium of required components of the effector system (e.g. complement). However, in serum, for example, either in vitro or in vivo all necessary components for effector function may be present ab initio, allowing effector function to be called down upon binding of the multi-specific binding substance to the target and to antibody.

A further aspect of the invention provides the use of a multi-specific binding substance in the recruitment of an antibody-mediated effector function to a target, the binding substance having an anti-antibody binding specificity and binding specificity for the target. The use may be made of the multi-specific binding substance in any method provided by the present invention. Use may be in the manufacture of a medicament for recruitment of antibody mediated effector function, e.g. for the treatment of a condition wherein this is, or is likely to be, of benefit (see above).

Pharmaceutical compositions comprising multi-specific binding substances as disclosed, and use of such compositions, are also provided by the present invention. Such pharmaceutical compositions may comprise any suitable pharmaceutically acceptable excipient.

Another aspect of the present invention provides a multi-specific (e.g. bispecific) binding substance e.g. "diabody" (as disclosed) having an anti-antibody binding specificity (and a binding specificity for a target). Such a multi-specific binding substance has a binding site with anti-antibody binding specificity and a binding site with binding specificity for a target, and comprises a multimer of polypeptides, each polypeptide having a first domain comprising a binding region of an immunoglobulin heavy chain variable region and a second domain comprising a binding region of an immunoglobulin light chain variable region, the binding sites being formed by association of a first domain of one polypeptide in the multimer with a second domain of another polypeptide in the multimer. In a diabody, the first domain of each polypeptide is unable to associate with the second domain of that polypeptide to form an antigen binding site. Compositions comprising such a multimer, e.g. pharmaceutical compositions which may include a pharmaceutically acceptable excipient, are also provided by the invention. The diabody may be a polypeptide dimer.

In addition to utility in the methods and compositions disclosed supra, such a multispecific binding substance finds utility in a further aspect of the present invention, namely, a general method of targeting or recruiting an antibody to a target for which the antibody has no binding specificity, either with or without associated effector function. For instance a multi-specific (e.g. bispecific) diabody may be used in agglutination assays.

Figure 2:
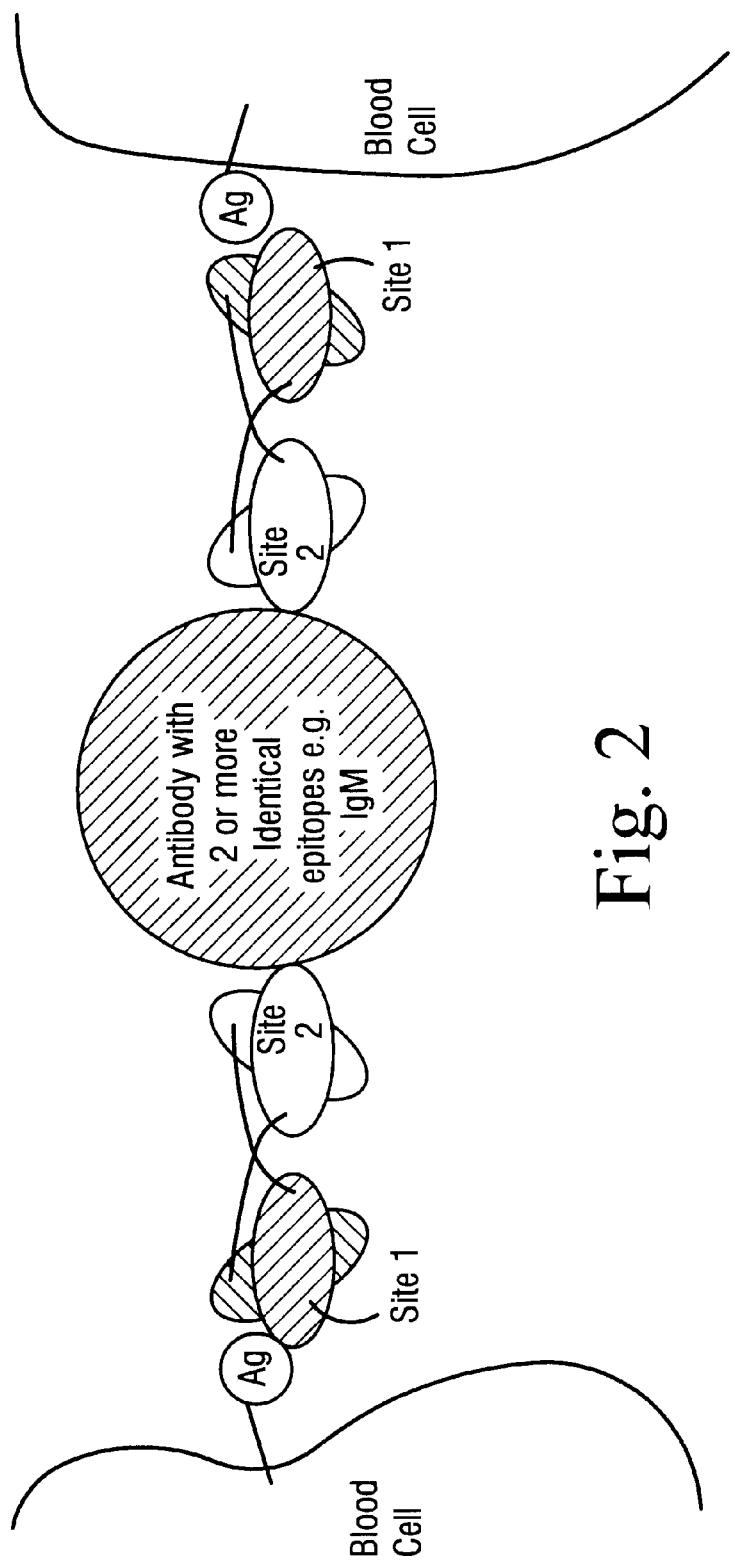

Multispecific binding substances such as the preferred diabodies (e.g. bispecific) may be used for coagulation of cells, bacteria or viruses, by making multiple interactions, as with diagnostic assays of agglutination of red blood cells, to determine for instance, blood cell types. Diabodies with one arm directed against an antibody molecule may be used in different formats to link together cells, as illustrated in FIG. 2.

For example, a diabody or other multi-specific binding substance may be used which has one arm directed against a cell surface antigen and another directed against IgM. The multivalent nature of IgM means that two or more diabody molecules may bind to the IgM molecule and thus crosslink between different blood cells. This IgM may be added as an extra reagent or it may be possible to use the IgM present in blood samples tested to promote the agglutination.

One arm may be directed against a cell surface antigen and the another directed against an idiotype commonly found in antibody molecules, such as antibodies directed against elements of the DP-47 VH gene, a gene segment commonly used in human antibodies (Tomlinson et al, *J. Mol. Biol.* 227 776–798 (1992)). IgM molecules with this idiotype would be particularly useful.

One arm may be directed against isotypes other than IgM for use in agglutination assays, but since these other antibodies are smaller, they may be less effective in agglutinating cells.

In any embodiment of the present invention the target may be any antigen e.g. of bacterial, viral, fungal, protozoal origin or antigen on the surface of cells (e.g. cancer cells), enabling recruitment of the natural antibody encoded effector functions to the targets displaying those antigens (e.g. bacteria, viruses, parasites or tumor cells) by way of a multi-specific binding substance which has binding specificity for the antigen and anti-antibody binding specificity.

Further aspects of the invention will be apparent to persons skilled in the art.

The following examples illustrate how the principles disclosed herein may be put into practice. Those skilled in the art will readily appreciate modifications and variations which may be made without departing from the invention disclosed herein.

All documents mentioned in the text are herein incorporated by reference.

FIG. 1 illustrates the use of a bispecific diabody to redirect an antibody such as IgG1 or IgM to a cell surface marker, triggering complement.

FIG. 2 illustrates the agglutination of red blood cells using a bispecific diabody directed against a blood cell antigen and an antibody, such as IgM with two or more identical epitopes. One diabody molecule binds to the blood cell antigen and to the IgM molecule. A second diabody molecule binds to the same IgM molecule and then binds to an antigen on a second blood cell, thus crosslinking and aggregating the blood cells.

EXAMPLE 1

Preparation and Characterisation of Bispecific Anti-2-phenyloxazol-5-one, Anti-mouse Lambda Light Chain Diabody A clone encoding a bispecific diabody directed against 2-phenyl-5-oxazolone and the mouse 1 light chain with a zero amino acid linker was prepared from DNA encoding an antibody against 2-phenyl-5-oxazolone derived from hybridoma NQ11 (anti-2-phenyloxazol-5-one; C. Berek is et al Nature 316 412–418, 1985; P. Holliger et al supra) and from DNA derived from a hybridoma LS136 directed against a mouse lambda light chain using the methodology essentially as described in example 1 of WO 94/13804. The bivalent diabody directed against the mouse lambda light chain was prepared as an intermediate step.

LS136 is a murine hybridoma directed against mouse antibody 1 light chains. It has been cloned in a diabody format using a 5 residue linker in the orientation VH-GGGGS-VL (SEQ ID NO:1) in the phagemid vector pUC119SfiNotmyc. The linker sequence was incorporated into the primer (VkCbaLinkSBstEII (SEQ ID NO:3) and primer4 (SEQ ID NO:7) (Table 1) used to amplify the 5' end of VK.Primer 4 also introduces a SacI restriction site at the 5' end of the VK. A restriction site for BstEII was incorporated 5' of the linker sequence of primer VkCbaLink5BstEII (SEQ ID NO:3) and primer4 (SEQ ID NO:7)and also at the 3' end of VH1FOR-2 (E. S. Ward, D. Gussow, A. D. Griffiths, P. T. Jones and G. Winter, Nature 341, 544–546 1989). This would allow the VH and linker-VL fragments to be cloned in a 3-way ligation reaction into the expression vector pUC119SfiNotmyc.

RNA was extracted from LS136 hybridoma cells and used to prepare cDNA. LS136 VH and VL domain DNA was amplified by PCR from cDNA using primers pairs VH3Aba and VH1FOR-2, and VkCbaLink5BstEII (SEQ ID NO:3) and VK4FOR (T. Clackson, H. R. Hoogenboom, A. D. Griffiths and G. Winter, Nature 352, 624–628 1991) respectively using standard conditions and reamplified by using VH3AbaSfi (SEQ ID NO:3) and VH1for-2 (for VH) and primer 4 (P. Holliger et al, supra) and Vk4foNot (for Vk). The product of the VH PCR reaction was digested with restriction enzymes SfiI and BstEII, and the product of the Vk PCR reaction was digested with restriction enzymes NotI and BstEII. The VH and the VL domain DNA was simultaneously ligated into SfiI/NotI digested pUC119SfiNotmyc in a molar ratio 3:3:1 (VH:VL:pUC119SfiNotmyc or pCantab6) and the resulting ligation mix used to transform E. coli TG1 cells. The VH and VL domain DNA was also ligated into Sfi/Not digested pCANTAB6 vector in the same way and transformed into E. coli HB2151 cells. Recombinants were screened for inserts of correct size using primers LMB2 (SEQ ID NO:11) and LMB3 (SEQ ID NO:12) for recombinants in the vector UCl19SfiNotmyc or LMB3 (SEQ ID NO:12) and fdSeq (SEQ ID NO:10) for recombinants in the vector pCANTAB6.

Expression of the LS136 Diabody

Soluble diabody was expressed by growth of the pUC119SfiNotmyc clone at 37° C. Cells in log phase growth in 2 mL 2YT/0.1% glucose/100 µMg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 µl ice cold PBS/1 mM EDTA and left on ice, 60 minutes. The cell suspension was centrifuged (1000 g for 10 minutes) and the diabody-containing supernatant used in ELISA as below.

50 µL periplasmic supernatant and 50 µL 3% BSA/PBS was added to ELISA wells coated with mouse IgMλ or mouse IgG2aλ (both from Sigma) (10 µg mL$^{-1}$ in PBS), blocked with 3% BSA/PBS. A standard ELISA protocol was followed (H. R. Hoogenboom et al., Nucl. Acids Res. 19, 4133–4137 1991) using detection of the myc-tag with the monoclonal antibody 9E10, and horseradish peroxidase conjugated anti mouse IgG (for IgMλ) and biotinylated anti mouse k chain and peroxidase-biotin-streptavidin complex (both Amersham) (for IgG2aλ1). ELISA readings after 10 minutes were greater than 1.0.

Construction of Bispecific Diabody LS136/NQ11/5 and Bispecific Diabody LS136/NQ11/0.

The two antibody specificities LS136 (anti-mouse λ antibody light chain) and NQ11 (anti-phOx) were combined in the bispecific diabody format fusing the VH and VL with a 5 amino acid linker VH-GGGGS-VL or directly with 0 linker in the orientation VH--VL in the phagemid vector pUC119SfiNotmyc. The linker sequence was incorporated into the primers 4 and 3 (Table 1; SEQ ID NOS:7& 6, respectively) used to amplify the 5' end of Vk and into the primers 7 and 6 (Table 1; SEQ ID NOS:9& 8, respectively) used to amplify the 3' end of VH. A restriction site for BstEII was incorporated 5' of the linker sequence of primer 3 and a restriction site for SacI was incorporated 5' of the linker sequence of primer 6. This would allow the assembled VH-linker and linker-VL fragments to be cloned in a 3-way ligation reaction into the expression vector pUC19LS136/5 BstEII/SacI.

Construction of the Bispecific Diabody LS136/NQ11/5 (5 Amino Acid Linker)

VHNQ11 was amplified with primers 2 and 7 (Table 1; SEQ ID NOS:5& 9, respectively), the VKNQ11 was amplified with the primers 1 and 4 (SEQ ID NOS:4& 7, respectively) using scFvNQ11 cloned into fdDOG-1 as template. The product of the VH PCR reaction was digested with restriction enzymes AscI and SacI, and the product of the VL PCR reaction was digested with restriction enzymes AscI and BstEII. A vector fragment of diabody LS136/5 (see above) was cut with BstEII/ SacI and the VH and the VL domain DNA were simultaneously ligated with it in a molar ratio 3:3:1 (VH:VL:pUC119-LS136/5). The resulting ligation mix used to transform E. coli TG1 cells. Recombinants were screened for inserts of correct size using primers LMB2 (SEQ ID NO:11) and LMB3 (SEQ ID NO:12) for PCR amplification of recombinant colonies.

Construction of the Bispecific Diabody LS136/NQ11/0 (Zero Amino Acid Linker)

VHNQ11 was amplified with primers 2 and 6 (Table 1;SEQ ID NOS:5& 8, respectively), the VkNQ11 was amplified with the primers 1 and 3 (SEQ ID NOS:4& 6, respectively) using scFvNQ11 cloned into fdDOG-1 as template. The product of the VH PCR reaction was digested with restriction enzymes AscI and SacI, and the product of the VL PCR reaction was digested with restriction enzymes AscI and BstEII. A vector fragment of diabody LS136/5 (see above) was cut with BstEII/SacI and the VH and the VL domain DNA were simultaneously ligated with it in a molar ratio 3:3:1 (VH:VL:pUC119-LS136/5). The resulting ligation mix used to transform E. coli TG1 cells. Recombinants were screened for inserts of correct size using primers LMB2 (SEQ ID NO:11) and LMB3 (SEQ ID NO:12) for PCR amplification of recombinant colonies.

Expression of Bispecific Diabody LS136/NQ11/5 and Bispecific Diabody LS136/NQ11/0

Soluble diabody was expressed by growth at 37° C. Cells in log phase growth in 2 mL 2YT/0.1% glucose/100 µg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 µl ice cold PBS/1 mM EDTA and left on ice, 60 minutes. The cell suspension was centrifuged (1000 g for 10 minutes) and the diabody-containing supernatant used in ELISA for λ light chain as above or for phOx as in example 1 of WO 94/13804. ELISA signals of greater than 1.0 were obtained after 10 min.

EXAMPLE 2

Preparation and Characterisation of Bispecific Anti-hen Egg Lysozyme, Anti-mouse Lambda Light Chain Diabody, and Demonstration of Complement Lysis A clone encoding a bispecific diabody directed against hen egg lysozyme (HEL) and the mouse λ light chain with a five and a zero amino acid linker was prepared from DNA encoding a single chain Fv antibody fragment against hen egg lysozyme (HEL) derived from the V genes from the anti-HEL antibody HyHEL10 (T. B. Lavoie, W. B. Drohan and S. J. Smith-Gill J. Immunol. 148 503–513 1992; gift of Sandra Smith-Gill) and from DNA derived from a hybridoma LS136 directed against a mouse lambda light chain using the methodology essentially as described in example 1 and P. Holliger et al (1993 supra) A bivalent diabody directed against the mouse lambda light chain described essentially as in example 1 was used as an intermediate step.

DNA encoding the VH and VL domains of the diabody was prepared and digested exactly as described in example 1 of WO 94/13804. The VH and VL domain DNA was simultaneously ligated into SfiI/Not I digested pCANTAB5-E (Pharmacia) in a molar ratio of 3:3:1 and the resulting ligation mix used to transform E.coli HB2151 cells. Recombinants were screened for inserts of the correct size using primers fdseq (SEQ ID NO:10) and LMB3(SEQ ID NO:12).

Expression of the LS136 Diabody

Soluble diabody was expressed by growth at 37° C. Cells in log phase growth in 2 mL 2YT/0.19 glucose/100 µg mL$^{-1}$ ampicillin were induced by adding IPTG to a final concentration of 1 mM IPTG and grown for 3 hours at 22° C. The cells were centrifuged (1000 g 10 minutes) and the cell pellet resuspended in 100 μl ice cold PBS/1 mM EDTA and left on ice, 60 minutes. The cell suspension was centrifuged (1000 g for 10 minutes) and the diabody-containing supernatant used in ELISA as below.

50 μL periplasmic supernatant and 50 μL 3% BSA/PBS was added to ELISA wells coated with mouse IgMλ or mouse IgG2aλ (both from Sigma) (10 μg mL$^{-1}$ in PBS), blocked with 3% BSA/PBS. A standard ELISA protocol was followed (H. R. Hoogenboom et al., Nucl. Acids Res. 19, 4133–4137 1991) using detection of the E-tag with the monoclonal anti-E tag antibody conjugated to HRP (Ray Mernaugh, Pharmacia) ELISA readings after 10 minutes were greater than 1.0.

Construction of Bispecific Diabody LS136/HyHEL10/5 and Bispecific Diabody LS136/HyHEL10/0

The two antibody specificities LS136 (anti-mouse λ antibody light chain) and HyHEL10 (anti-lysozyme) were combined in the bispecific diabody format fusing the VH and VL domains with a 5 amino acid linker VH-GGGGS-VL or directly with 0 linker in the orientation VH--VL in the phagemid vector pCANTAB5-E (Pharmacia). The linker sequence was incorporated into the primers 3 and 4 (Table 1; SEQ ID NOS:6& 7, respectively) used to amplify the 5' end of Vk and into the primers 6 and 7 (Table 1; SEQ ID NOS:8& 9, respectively) used to amplify the 3' end of VH. A restriction site for BstEII was incorporated 5' of the linker sequence of primers 3 and 4 and a restriction site for SacI was incorporated 5' of the linker sequence of primer 6 and 7. This would allow the assembled VH-linker and linker-VL fragments to be cloned in a 3-way ligation reaction into the expression vector pCANTABS-E LS136/5 BstEII/SacI.

Construction of the Bispecific Diabodies LS136/ HyHEL10/5 (5 Amino Acid Linker)

VHHyHEL10 was amplified with primers 2 and 7 (Table 1; SEQ ID NOS:5& 9, respectively) and VkHyHEL10 was amplified with the primers 1 (SEQ ID NO:4) and 4 (SEQ ID NO:7) for the 5 amino acid linker diabody LS136/ HyHEL10/5 using scFvHyHEL10 cloned into pUC119 as template. The product of the VH PCR reaction was digested with restriction enzymes AscI and SacI, and the product of the VL PCR reaction was digested with restriction enzymes AscI and BstEII. A vector fragment of diabody LS136/5 (see above) was cut with BstEII/SacI and the VH and the VL domain-DNA were simultaneously ligated with it in a molar ratio 3:3:1 (VH:VL.pCANTAB5-E LS136/5) The resulting ligation mix used to transform E. coli HB2151 cells. Recombinants were screened for inserts of correct size using primers fdseq (SEQ ID NO:10) and LMB3 (SEQ ID NO:12) for PCR amplification of recombinant colonies.

Construction of the Bispecific Diabody LS136/HyHEL10/0 (Zero Amino Acid Linker)

VHHyHEL10,was amplified with primers 2 and 6 (Table 1; SEQ ID NOS:5& 8, respectively), the VkHyHEL10 was amplified with the primers 1 (SEQ ID NO:4) and 3 (SEQ ID NO:6) using scFvHyHEL10 cloned into pUC119 as template. The product of the VH PCR reaction was digested with restriction enzymes AscI and SacI, and the product of the VL PCR reaction was digested with restriction enzymes AscI and BstEII. A vector fragment of diabody LS136/5 (see above) was cut with BstEII/SacI and the VH and the VL domain DNA were simultaneously ligated with it in a molar ratio 3:3:1 (VH:VL:ppCANTAB5-E-LS136/5).The resulting ligation mix used to transform E. coli HB2151 cells. Recombinants were screened for inserts of correct size using primers fdSeq (SEQ ID NO:10) and LMB3, (SEQ ID NO:12) for PCR amplification of recombinant colonies.

Expression of Bispecific Diabody LS136/HyHEL10/5 and Bispecific Diabody LS136/HyHEL10/0

Soluble diabody was expressed by growth at 37° C. Cells in log phase growth in 2 mL 2YT/0.1% glucose/100 μg mL$^{-1}$ ampicillin were induced by adding IPTG to a final concentration of 1 mM IPTG and grown 3 hours 22° C. The cells were centrifuged (1000 g 10 minutes) and the cell pellet resuspended in 100 μl ice cold PBS/1 mM EDTA and left on ice, 60 minutes. The cell suspension was centrifuged (1000 g for 10 minutes) and the diabody-containing supernatant used in ELISA for λ light chain as above or for hen egg lysozyme as in P. Holliger et al (Proc. Natl. Acad. Sci. USA 90 6444–6448), 1993. ELISA signals of greater than 1.0 were obtained after 10 min.

Expression of LS136/HyHEL105 Diabody for Purification and Complement Lysis Assay Soluble diabody was expressed by growth at 37° C. Cells in log phase growth in 2 mL 2YT/0.1% glucose/100 μg mL$^{-1}$ ampicillin were induced by adding IPTG to a final concentration of 1 mM IPTG and grown for 24 hours at 22° C. The cells were centrifuged (1000 g for 10 min) and the cell pellet resuspended and supernatant filtered through a 0.16 μm filter and concentrated by cross-flow filtration (filter cutoff 10 kD). The concentrate was purified on a HEL-Sepharose affinity column. The column was washed with 10 column volumes of PBS, 5 column volumes of 0.5M NaCl/ 0.1 mM Tris, pH8.5 and protein was eluted with 100 mM triethylamine into ice-cold 1M Tris, pH7.5 and dialysed extensively against PBS/0.2 mM EDTA.

Complement Lysis Assay

The ability of the LS136/HyHEL10/5 diabody to retarget antibodies and utilise their effector functions was determined using a complement lysis assay.

Preparation of Lysozyme Coated Red Blood Cells

Human red blood cells (RBC's) were used for this technique. Having removed and discarded the buffy coat from the red blood cells, they were washed, spun down and resuspended four times with PBS, each time discarding the supernatant. It was important not to mix cells of different blood groups prior to this washing stage. After the final wash and spin, the packed RBC's were coated with protein by mixing RBC's, coating protein solution (10 mg/ml lysozyme in PBS) and 1-ethyl-3-(3-dimethylaminopropyl) carbodiimide (EDAC; 100 mg/ml in PBS) in the ratio 1:4:1 (v/v). This mixture was turned end over end on a rotating platform at 4° C. for 1.5 hours after which the RBCs were spun down and the supernatant removed and discarded. Subsequently, the cells were washed 5 times in approximately 10 ml PBS (until there was no further haemolysis) and then resuspended in a final volume of 10 ml PBS ready for use.

Complement Lysis Assay

Red blood cells coated with 10 mg/ml HEL were washed three times in complement fixation diluent (Oxoid, Basingstoke) and 50 μl of a 1% suspension added to wells of a 96 well microtitre plate. Dilutions of the purified diabody LS136/HyHEL10/5 (from 1 mg/ml to 10 ng/ml; 50 μl) were added and incubated for 20 min at room temperature. The cells were pelleted by a centrifugation at 2000 rpm for 5 minutes and the supernatant was discarded. The cells were resuspended in dilutions of an immunoglobulin IgM with a lambda light chain (IgMλ) that is not specific for an antigen in the assay (Myeloma MOPC 104E) and incubated for 20 minutes at room temperature. The cells were again pelleted by a centrifugation at 2000 rpm for 5 min and the supernatant was discarded. Now the cell pellet was washed once with complement fixation diluent and the cells were pelleted again and resuspended in a 1 in 20 dilution of guinea pig complement (prepared from guinea pig serum after agglutination of red blood cells and incubated for 30 minutes at 37° C. Cell debris was pelleted by a centrifugation at 4000 rpm for 5 minutes and the supernatant was transferred to another microtitre plate and the absorbance at 405 nm was read.

The degree of lysis was found to titrate with both dilutions of the LS136/HYHEL10/5 diabody and of the Myeloma MOPC 104E IgMλ. A combination of 50 µg/ml of IgMλ and 10 ng/ml of diabody was found to give 50% of maximum lysis of HEL coated red blood cells. No lysis (apart from background lysis) was observed using non-coated or phOx-BSA coated red blood cells or leaving out either the diabody or the IgMλ.

Similar results were obtained when the ability of the diabody to retarget IgG2aλ and antibodies from whole serum was determined using the complement lysis assay. The same standard assay was performed using 50 ng/ml of the LS136/HyHEL10/5 diabody and an immunoglobulin IgG2a with a lambda light chain (IgG2aλ) that is not specific for the antigen in the assay (Myeloma HOPC-1) (100 µg/ml). The diabody was found to direct efficiently complement induced hemolysis in this case.

The complement assay was also performed by simply mixing antigen-coated red blood cells, diabody and IgMλ in a volume of 150 µl of guinea pig complement, diluted ⅕ in complement fixation diluent. Efficient hemolysis was again observed after incubation at 37° C. for 30 minutes. In the absence of diabody this assay set up resulted in some background hemolysis.

We conclude therefore that the diabody is effective in retargetting antibody effector functions of antibodies not specific for the antigen to cells with the antigen on their surface.

EXAMPLE 3

Preparation and Characterisation af an Anti-CEA, Anti-mouse Lambda Light Chain Diabody and Demonstration of Complement Mediated Lysis of a Tumour Cell A clone encoding a bispecific diabody directed against carcinoembryonic antigen (CEA) and the mouse λ light chain with a five amino acid linker was prepared from DNA encoding the variable regions derived from the murine anti-CEA antibody MFE23 which binds the tumour specific antigen carcinoembryonic antigen (CEA) and from the DNA derived from a hybridoma LS136 directed against a mouse lambda light chain using the methodology essentially as described in example 1 and P. Holliger et al (1993 supra). A bivalent diabody directed against the mouse lambda light chain described in examples 1 and 2 was used as an intermediate step in the construction.

Construction of a Bispecific Diabody LS136/MFE23/5

The two antibody specificities LS136 (anti-mouse λ antibody light chain) and MFE23 (anti-CEA) were combined in the bispecific diabody format fusing the VH and VL domains with a 5 amino acid linker VH-GGGGS-VL in the vector p-CANTAB5-E (Pharmacia). The linker sequence was incorporated into primer 4 (SEQ ID NO:7) used to amplify the 5' end of Vk and into primer 7 (SEQ ID NO:9) used to amplify the 3' end of VH. A restriction site for BstEII was incorporated 5' of the linker sequence of primer 4 and a restriction site for SacI was incorporated 5' of the linker sequence of primer 7. This would allow the assembled VH-linker and linker-VL fragments to be cloned in a 3-way ligation reaction into the expression vector pCANTAB-5E LS136/5 BstEII/SacI.

The MFE23 anti-CEA scFv clone described in PCT/GB93/02492 was first mutated to remove an internal BstEII site in the VL domain by in vitro mutagenesis using oligonucleotide CEA23-BstE (Table 1; SEQ ID NO:13) and the Sculptor kit (Amersham International). VHMFE23 was amplified with primers 2) and 7 (Table 1; SEQ ID NOS:5& 9, respectively) and VkMFE23 was amplified with primers 1 (SEQ ID NO:4) and 4 (SEQ ID NO:7) for the 5 aminoacid linker diabody LS136/MFE23/5 using the mutated MFE23 anti-CEA scFv as template. The product of the VH .PCR reaction was digested with restriction enzymes AscI and SacI, and the product of the VL PCR reaction was digested with restriction enzymes AscI and BstEII. Vector pCANTAB-5E DNA encoding the diabody LS136/5 (see above) was cut with BstEII/ SacI and the VH and the VL domain DNA was simultaneously ligated with it in a molar ratio 3:3:1 (VH:VL:pCANTAB5-E LS136/5). The resulting ligation mix was used to transform E. coli HB2151 cells. Recombinants were screened for inserts of correct size using primers fdseq (SEQ ID NO:10) and LMB3 (SEQ ID NO:12) for PCR amplification of recombinant colonies. The SfiI-NotI fragment encoding the diabody was then subcloned into the vector pUC119 SfiNot-hismyc for expression.

Expression of Bispecific Diabody LS136/MFE23/5

Soluble diabody was expressed by growth at 37° C. Cells in log phase growth in 2 mL 2YT/0.1% glucose/100 µg mL$^{-1}$ ampicillin were induced by adding IPTG to a final concentration of 1 mM IPTG and grown for 3 hours 22° C. The cells are centrifuged (100 g 10 minutes) and the cell pellet resuspended in 100 µl ice cold PBS/1 mM EDTA and left on ice, 60 minutes. The cell suspension was centrifuged (1000 g for 10 minutes) and the diabody-containing supernatant used in ELISA for λ light chain as in examples 1 and 2 or for CEA as described by A. D. Griffiths et al (EMBO J. 12 725–734, 1993). ELISA signals of greater than 1.0 were obtained after 10 min.

Expression of LS136/MFE23/5 Diabody for Purification and Complement Lysis Assay

Soluble diabody was expressed by growth at 37° C. Cells in log phase growth in 2 mL 2YT/0.1% glucose/100 µg mL$^{-1}$ ampicillin are induced by adding IPTG to a final concentration of 1 mM IPTG and grown for 24 hours at 22° C. The cells were centrifuged (1000 g for 10 min) and the cell pellet resuspended and supernatant filtered through a 0.16 µm filter and concentrated by cross-flow filtration (filter cutoff 10 kD). The concentrate was purified using immobilised metal affinity chromatography (IMAC) using nickel-NTA agarose (Qiagen cat. no. 30210) using the manufacturer's instructions and dialysed extensively against PBS/EDTA.

Complement Lysis Assay

The ability of the LS136/MFE23/5 diabody to retarget antibodies and utilise their effector functions is determined using a complement lysis assay using Chromium ($^{51}$Cr) release.

2×10$^6$ LS 174T target cells (ATCC CL 188, U.S. Pat. No. 4,288,236) are harvested after desorption and washed with RPMI 1640 medium containing 10% fetal calf serum. After centrifugation of the cells the pellet is labelled with $^{51}$Cr (200 µCi) for 1 hour at 37° C. After 2 washes in RPMI 1640 medium the target cells (5000 cells per assay) are aliquotted into culture wells.

Dilutions of the purified diabody LS136/MFE23/5 (from 1 mg/ml to 10 ng/ml; 50 µl) are added and incubated for 20 min at room temperature. The cells are pelleted by a centrifugation at 2000 rpm for 5 minutes and the supernatant discarded. The cells are resuspended in dilutions of an immunoglobulin IgM with a lambda light chain (IgMλ) that is not specific for an antigen in the assay (Myeloma MOPC 104E) and incubated for 20 minutes at room temperature. The cells are again pelleted by a centrifugation at 2000 rpm for 5 min and the supernatant discarded. Now the cell pellet is washed once with complement fixation diluent and the cells are pelleted again and resuspended in a 1 in 20 dilution of guinea pig complement (prepared from guinea pig serum after agglutination of red blood cells) and incubated for 30 minutes at 37° C. Cell debris is pelleted by a centrifugation at 4000 rpm for 5 minutes and the supernatant was transferred to another microtitre plate The cells are spun and half the supernatant (100 μl) is collected and chromium release is determined in a gamma counter. Each sample point is done in triplicate and the percentage of specific lysis is calculated as:

100×(Mean sample release−spontaneous release)/(maximum release−spontaneous release)

Spontaneous release is measured from target cells in assay medium alone and maximum release is measured after lysis of an equivalent number of target cells in 1M HCl.

The degree of lysis is found to titrate with both dilutions of the LS136/MFE23/5 diabody and of the Myeloma MOPC 104E IgMλ. No lysis (apart from background lysis) is observed leaving out either the diabody or the IgMλ or using a phOx-ESA coated red blood cell control in place of the tumour cell.

EXAMPLE 4

Lysis of a Tumour Cell by Antibody Directed Cell-mediated Cytotoxicity Directed by a Diabody Directed Against CEA and a Mouse Lambda Light Chain ADCC is a natural antibody encoded effector function brought about by binding of antibody Fc region to Fc receptors. Cells coated by antibodies are killed through lysis by a range of mononuclear cells.

Mononuclear cells were isolated from Balb/c mose spleen on Ficoll gradient and grown for 3 days in RPMI (Russel Park Memorial Institute)/10% Fetal calf serum (FCS) at 37° C. in tissue culture flasks pretreated with a mitogenic anti-CD3 antibody (e.g. 2C11 at 50 μg/ml in PBS for 24 h and washed 4 times with PBS to remove unbound antibody). Then they were transferred to untreated flasks for 3–7 days for expansion in RPMI/5% FCS and 10 units /ml recombinant interleukin 2 (IL-2) at 37° C.

$2 \times 10^6$ LS 174T target cells (ATCC CL 188, U.S. Pat. No. 4,288,236) are harvested after desorption and washed with RPMI 1640 medium containing 10% fetal calf serum. After centrifugation of the cells the pellet is labelled with $^{51}Cr$ (200 μCi) for 1 hour at 37° C. After 2 washes in RPMI 1640 medium the target cells (5000 cells per assay) are aliquotted into culture wells.

Dilutions of the purified diabody LS136/MFE23/5 (from 1 mg/ml to 10 ng/ml; 50 μl) are added and incubated for 20 min at room temperature. The cells are pelleted by a centrifugation at 2000 rpm for 5 minutes and the supernatant discarded. The cells are resuspended in dilutions of an immunoglobulin IgG1 with a lambda light chain (IgG1λ) that is not specific for an antigen in the assay (Myeloma 3C52'CL: anti-4-hydroxy-3-phenylacetyl (NIP)) and incubated for 20 minutes at room temperature. The cells are again pelleted by a centrifugation at 2000 rpm for 5 min and the supernatant discarded.

K-cells were washed to remove IL-2 and are then added to give effector:target (K-cells:LS174T) ratios between 50:1 and 10:1 and incubated for 4 h at 37° C. The cells were spun and half the supernatant (100 μl) is collected and chromium ($^{51}Cr$) release is determined in a gamma counter. Each sample point is done in triplicate and the percentage of specific lysis is calculated as:

100 ×(Mean sample release−spontaneous release)/(maximum release−spontaneous release)

Spontaneous release is measured from target cells in assay medium alone and maximum release is measured after lysis of an equivalent number of target cells in 1M HCl. The degree of lysis is found to titrate with both dilutions of the LS136/MFE23/5 diabody and of the Myeloma 3C52'CL IgG1λ. No lysis (apart from background lysis) is observed leaving out either the diabody or the IgG1λ, or using a phOx-BSA coated red blood cell control in place of the tumour cell.

Thus the diabody can retarget the ADCC activity triggered by the IgG1λ antibody to a tumour cell encoding an antigen to which one arm of the diabody is directed.

EXAMPLE 5

In vivo Retargetting of Antibody to Mediate Turnover Lysis

The bispecific diabody LS136/MFE23/5 is useful for treatment of a xenografted $CEA^+$adenocarcinoma LS174T in nude mice.

Nude mice lack T-cells and allow the growth of xenografted human tumors. They do however have normal B-cells and normal serum Ig levels and they show normal T-independent immune responses e.g. some antibody responses.

For in vivo application diabody is expressed and purified as described in Ex 3. and additionally purified on Pharmacia Superdex7™ 16/60 seizing column to remove endotoxin (LPS).

Balb/c nude mice are injected (for example i.v.) with a significant number of LS174T tumour cells (e.g. 5000) on day one are treated with single or muliple i.v. injections of the desired amount of diabody (e.g. 100 μg) in phosphate buffered saline (PBS) at a later point in time. In this setup, serum Ig is in excess to the diabody and consequently the great majority of Ig will only complex with one diabody.

In an alternative protocol, more than one diabody complexes with any species of serum Ig in order to have advantages high avidity binding to the target antigen. This may be achieved by incubation with serum Ig prior to injection. Removal of a convenient amount of serum from the mouse (e.g. 100 μl, total serum Ig λ concentrations in naiveBalb/c mouse is <1 mg/ml)) is followed by addition of the desired amount of diabody (e.g. 100 μg) in phosphate buffered saline (PBS), in vitro mixing and incubation of serum and diabody to allow diabody to bind to serum Ig prior to reinfusion into the mouse.

The bispecifc LS136/MFE23/5 diabody targets λ light chain bearing Ig. which amounts to <5% of total serum Ig.

However the level of serum Ig λ can be greatly boosted by immunisation with certain antigens that elicit T-cell independent responses e.g. dextran. The efficiency of treatment regimes (as described above) may be increased if Ig λ levels are boosted in such a way prior to administration of the diabody.

It is worth noting that in this case too the recruited antibody specificities are not directed against the target antigen as immunization is done with irrevelvant antigens.

TABLE 1

Oligonucleotides used

VH3AbaSti

```
5'-CAT GCC ATG ACT CGC GGC CCA GCC GGC CAT
   GGC CSA GGT GAA GCT GGT GGA RTC TGG-3'
```
VKCbaLink5BStE

```
5'-GAG CCA TCA ATC GAT CTG GTC ACC GTC TCC
   TCA GGC GGT GGC GGA TCG GAC ATT GTG CTR ACC
   CAG TCT CCA-3'
```
Primer 1:

```
5'-GAC TCA TTC TCG ACT GAG CTC ACT TGG CGC
   GCC TTA TTA CCG TTT GAT CTC GAG CTT GGT CCC-3'
```
Primer 2:

```
5'-GTC CTC GCA ACT GGC GCG CCA CAA TTT CAC
   AGT AAG GAG GTT TAA CTT GTG AAA AAA TTA TTA
   TTC GCA ATT-3'
```
Primer 3:

```
5'-GAG CCA TCA ATC GAT CTG GTC ACC GTC TCC
   TCA GAC ATT GAG CTC ACC CAG TCT CCA-3'
```

TABLE 1-continued

Oligonucleotides used

Primer 4:

```
5'-GAG CCA TCA ATC GAT CTG GTC ACC GTC TCC
   TCA GGC GGT GGC GGA TCG GAC ATT GAG CTC ACC
   CAG TCT CCA-3'
```
Primer 6:

```
5'-GAG CCA TCA ATC TCG GAG CTC GAT GTC TGA
   GGA GAC GGT GAC CGT GGT CCC TTG GCC CC-3'
```
Primer 7:

```
5'-GAG CCA TCA ATC TCG GAG CTC GAT GTC CGA
   TCC GCC ACC GCC TGA GGA GAC GGT GAC CGT GGT
   CCC TTG GCC CC-3'
```
fdSEQ

```
5'-GTC GTC TTT CCA GAC GTT AGT-3'
```
LMB 2

```
5'-GTA AAA CGA CGG CCA GT-3'
```
LMB 3

```
5'-CAG GAA ACA GCT ATG AC-3'
```
CEA3-BstE

```
5'-GGT TAT GGT GAC TTT CTC CCC-3'
```

---

What is claimed is:

1. A method of recruiting an antibody-mediated effector function to an antigenic target in an individual, the method comprising:

binding a multi-specific binding molecule, said multi-specific binding molecule comprising at least two antibody variable domains each with an antigen binding site wherein one antigen binding site has binding specificity for antibodies native to the serum of said individual ("native antibodies") and wherein the other said antigen binding site has non-covalent binding specificity for the antigenic target, to said native antibodies and said antigenic target and causing or allowing the native antibodies thus bound to mediate their effector function, wherein said native antibodies which are bound include antibodies which do not necessarily possess specificity for said antigenic target.

2. A method according to claim 1 wherein the binding specificity of the molecule for antibodies is isotype specific.

3. A method according to claim 2 wherein the binding specificity of the molecule for antibodies is for the constant region of one or more isotypes.

4. A method according to claim 3 wherein the target is a human cell.

5. A method according to claim 2 wherein the target is a human cell.

6. A method according to claim 1 wherein the target is a human cell.

7. A method according to claim 1 wherein the binding molecule comprises a multimer of polypeptides, each polypeptide having a first domain comprising a binding region of an immunoglobulin heavy chain variable region and a second domain comprising a binding region of an immunoglobulin light chain variable region, association of a first domain of one polypeptide in the multimer and a second domain of a second polypeptide within the multimer forming an antigen binding site.

8. A method according to claim 7 wherein the first domain of each polypeptide is unable to associate with the second domain of that polypeptide to form an antigen binding site.

9. A method according to claim 8 wherein the target is a human cell.

10. A method according to claim 7 wherein the target is a human cell.

11. A multi-specific binding molecule which has a first binding site with anti-antibody specificity and a second binding site with non-covalent binding specificity for an antigens target, and which comprises a multimer of polypeptides, each polypeptide having a first domain comprising a binding region of an immunoglobulin heavy chain variable region and a second domain comprising a binding domain of an immunoglobulin light chain variable region, the binding sites formed by association of a first domain of one polypeptide in the multimer with a second domain of another polypeptide in the multimer, the first binding site being for a human antibody such that binding of the molecule to the antigenic target and said human antibody provides for the human antibody to mediate its effector function on said target.

12. A binding molecule according to claim 11 wherein the first domain of each polypeptide is unable to associate with the second domain of that polypeptide to form an antigen binding site.

13. A method of binding an antibody to a target for which the antibody has no binding specificity, comprising binding a multi-specific binding molecule according to claim 11 or 12 to an antibody and to the target.

14. A method of binding an antibody to a target for which the antibody has no binding specificity, comprising binding a multi-specific binding molecule according to claim 12 to an antibody and to the target.

15. A multispecific binding molecule according to claim 11 wherein said multimer is a dimer, the binding site with anti-antibody specificity binds to the constant ($C\mu$) region of IgM and the binding site with non-covalent binding specificity for an antigenic target binds to a blood cell surface antigen.

* * * * *